United States Patent [19]

Schmidt

[11] Patent Number: 4,849,246

[45] Date of Patent: Jul. 18, 1989

[54] PROCESS FOR PRODUCING AN ADMINISTRATION OR DOSAGE FORM FOR DRUGS, REAGENTS OR OTHER ACTIVE INGREDIENTS

[76] Inventor: Wolfgang Schmidt, Reembroden 44, D-2000 Hamburg 63, Fed. Rep. of Germany

[21] Appl. No.: 60,689

[22] PCT Filed: Oct. 7, 1986

[86] PCT No.: PCT/EP86/00571

§ 371 Date: Jun. 9, 1987

§ 102(e) Date: Jun. 9, 1987

[87] PCT Pub. No.: WO87/02241

PCT Pub. Date: Apr. 23, 1987

[30] Foreign Application Priority Data

Oct. 9, 1985 [DE] Fed. Rep. of Germany ....... 3536024

[51] Int. Cl.$^4$ .................. A01W 1/02; A61K 9/00; A61K 15/00; A61K 21/00
[52] U.S. Cl. ..................................... 427/2; 424/478; 424/479; 427/3
[58] Field of Search ............... 427/2, 3; 424/478, 479

[56] References Cited

U.S. PATENT DOCUMENTS 3,444,858  5/1969  Russell ..................... 128/260

FOREIGN PATENT DOCUMENTS 2746414  4/1979  Fed. Rep. of Germany .
51-54917  6/1976  Japan .
139077  2/1920  United Kingdom .
1061557  3/1967  United Kingdom .

OTHER PUBLICATIONS

Chemical Abstracts, vol. 85, 1976, p. 364.

*Primary Examiner*—Michael Lusignan
*Attorney, Agent, or Firm*—Cushman, Darby & Cushman

[57] ABSTRACT

A process for producing an administration or dosage form of drugs, reagents or other active ingredients. A watersoluble foil composed of starch, gelatin, glycerin and/or sorbit and if necessary other additives is coated by a roll coating process with a layer containing the active ingredients and composed of the same basic ingredients. After a corresponding prefragmentation, the administration form thus produced is particularly useful as an oral administration drug.

15 Claims, No Drawings

PROCESS FOR PRODUCING AN ADMINISTRATION OR DOSAGE FORM FOR DRUGS, REAGENTS OR OTHER ACTIVE INGREDIENTS

Drugs or pharmaceuticals can be orally administered in the form of powders, dropping solutions or juices. As precise dosing is difficult with such administration forms, preference is generally given to manufacturer-dosed administration forms such as tablets, dragees or capsules. Reagents and other active ingredients, e.g. sweeteners or flavouring agents are frequently also tableted for a precisely dosed administration. The production procedure for tablets, dragees, capsules, etc. has largely been completely developed, but it is not possible to overlook a number of system-related disadvantages.

For low-dosed active ingredients, a large proportion of adjuvants must be added in order to obtain a handlable size of the individual dose. It is also substantially impossible to precisely mark individual tablets or dragees. Therefore blister packs have been adopted, which contain a large number of tablets, dragees and also capsules and which are printed with the necessary information and in particular the product name. The manufacture of such packs naturally involves an additional operation and pack transfers in the form of folding boxes are required, which have a considerable empty volume and therefore take up additional storage space. Another serious disadvantage of dragees and capsules is that splitting up is not possible, so that the minimum dose is predetermined. An accurate breaking up is also difficult in the case of tablets and only larger tablets provided with a notch as a predetermined breaking point can be split, but frequently fragments of unequal size are obtained.

Attempts have already been made to find a new administration form for the oral administration of drugs in the form of active ingredient-containing films or foils. Belgian Pat. No. 637,363 discloses a paper-like support material of insoluble cellulose fibres impregnated with an active ingredient solution or coated by application or sprinkling, dosing being achieved by perforating the support film in the manner of a sheet of postage stamps. The dosing of the active ingredient is necessarily extremely imprecise. DE-OS No. 24 32 925 and DE-OS No. 24 49 865 disclose the incorporation of drug active ingredients into film forming agents, which are preferably in the form of water-soluble compounds, such as methyl and ethyl cellulose, but in particular hydroxypropyl cellulose, hydroxyethyl cellulose or methylhydroxypropyl cellulose. The films can also contain fillers and parting agents. The thus obtained active ingredient-containing films can also be subdivided into individual portions by perforation for dosing purposes.

However, these proposals have not led to practical adoption and in the latest text book "Arzneiformenlehre" by P.H. List, fourth edition, Stuttgart 1985, no mention is made thereof. This is clearly based on the fact that the hitherto known proposals do not make it possible to obtain the requisite constant weight and uniform active ingredient distribution, such as are nowadays required. The Pharmakopoea Europae e.g. sets criteria for the uniformity of the weight of individually dosed drugs, which are graded according to the maximum permitted variations in per cent corresponding to the particular average weight. This requirement is generally ±5 to max. 10%. Corresponding values exist for solid drugs with respect to other parameters, such as the disintegration time and dissolving rate.

The aforementioned prior art proposals lead to products with an inadequate acceptance by the patient (e.g. it is difficult to ingest paper portions) and do not permit an accurate dosing per surface unit, as is an absolute requirement. When incorporating the active ingredient into a film, difficulties are caused not only by the precise dosing, but also it is necessary to produce a separate film for each active ingredient, so that the production process is not economic.

The problem of the present invention is to provide a "two-dimensional" administration and dosage form, which does not suffer from the aforementioned disadvantages, which can be easily produced and can be very flexibly adapted to the requirements of the market and different active ingredients.

The invention therefore relates to a process for the production of an administration and dosage form for drug active ingredients, reagents or other active ingredients in the form of a film with an active ingredient-containing coating, which is characterized in that.

(a) a water-soluble support film is produced from an aqueous composition based on starches, gelatins, glycerol and/or sorbitol, as well as optionally natural and/or synthetic resins and/or gums, (b) an aqueous coating material is prepared from the active ingredient, as well as starches, gelatins, glycerol and/or sorbitol, as well as optionally natural and/or synthetic resins and/or gums, and (c) the coating material is continuously applied by means of a roll coating process and in a precisely predetermined quantity (coating thickness) to at least one side of the support film.

The inventively produced administration form has a large number of important advantages:

One support film can be used for the most varied active ingredients and can therefore be economically produced in larger numbers.

The active ingredient-containing coating can be very thin in the case of very efficaceous drugs, because the support material ensures an adequate mechanical strength.

With the aid of modern roll application processes the active ingredient-containing coating can be applied with a constant thickness, so that the necessary tolerances can be respected.

If sterilization is necessary, this can be achieved without difficulty by radiation treatment due to the limited coating thickness.

The support can be printed with different information on the front and in particular rear surface using physiologically acceptable printing inks.

As a result of the relatively large surface area of e.g. 4 to 10 $cm^2$, detailed information for the user can be printed on the uncoated support material, or even subsequently.

The dosage units can be rendered flexible by a corresponding pre-separation, e.g. by perforation, so that it is only necessary to produce one product for different dosages (e.g. for adults and children); whereby the pre-separation can optionally be carried out in the pharmacists or hospital in accordance with details provided by the doctor.

The inventive administration form shares the common advantage of the known film-form administration forms of extremely small space requirements. Thus, in place of folding boxes, it is e.g. possible to use pouches or bags made from plastic film or plastic-coated paper, into which the product is sealed, in much the same way as moist refreshing cloths.

The support film is manufactured in per se known manner using a continuously operating roll-based film machine. The coating process for producing the support film is based on the roller principle, i.e. the aqueous composition for the support film is applied by means of rolls and doctor blades and spread out to form thin webs, predried on the rolls and then in the main drying process subsequently dried to the desired final moisture content. The end product obtained is so strong and elastic that it can be wound onto reels and stored, if the residual moisture content is not too high (risk of mould formation).

The width of the film can be of a random nature and is advantageously adapted to the coating machine width. It is obvious to adapt the two widths to one another at the time of manufacture. It is technically also possible to carry out film production and coating in time succession on the same plant, which significantly improves the economics of the process.

The composition used is kept at the desired temperature, viscosity and homogeneity, accompanied by pumping round. The film is subsequently dried in a heating tunnel. The thus obtained support film constitutes the inert support for the subsequent coating with the different coating materials.

A physiologically unobjectionable composition is used for producing the water-soluble support film. The "water solubility" is to be defined in such a way that the film is produced from an aqueous composition and the finished film subsequently dissolves or swells during use in water or in gastric juice.

The film formers are in particular gelatins, as well as starches (potato starch, wheat starch, corn starch), as well as polyvinyl-pyrrolidone (PVP), methyl and ethyl cellulose, as well as polyvinyl alcohol (PVA). It is also possible to use water-soluble acrylic resin dispersions. Suitable plasticizers are in particular polyfunctional alcohols, such as glycerol and sorbitol (Karion).

The components are appropriately cold mixed with water and accompanied by slight heating and constant stirring are processed to a coatable slime. The stirring in of air must be avoided to the greatest possible extent, in order to obtain a clear, but slight opalescent material.

The thickness of the support film is preferably between approximately 50 and 250 μm. It can be controlled to a considerable extent. The characteristics of the support film can undergo significant quality influences by corresponding combination of film formers and plasticizers. The support film must have a uniform thickness (preferably e.g. 100 μm), must be slightly elastic and bendable, but without breaking. The starch proportion should be adequately high, so that moisture is absorbed on applying the coating material, without there being any sticking of the surface or softening of the complete film.

The following basic formulation has proved satisfactory for the support film:
  Gelatin 8 to 10 g
  Starch 4 to 8 g
  Glycerol 1 to 2 g
  Polyvinylpyrrolidone 1 to 2 g
  Water 30 to 50 g Water-soluble natural and/or synthetic resins, e.g. acrylic resins and gums are also suitable. It is also possible to add to the material other conventional substances, e.g. preservatives, such as p-hydroxybenzoates, inert soluble or insoluble fillers, sugar or other sweeteners, other polyols, waxes or dyes.

The possibility of printing the front and back of the support film is a particular advantage of the inventive administration form. For example, it is possible to print on the marking, details on the constituents, together with dosage details. It is optionally even possible to print on the back the entire content of a pack-in label, thereby rendering superfluous the need for such a separate label, which is frequently lost. In the case of drugs or pharmaceuticals which are regularly taken, e.g. in the case of hormonal contraceptives, the complete administration program can be given in such a way that it is possible to simply check the taking thereof. For printing purposes it is necessary to use physiologically acceptable inks (food colours), because the support film forms part of the orally administered administration form.

The active ingredient-containing coating material is an aqueous composition, which is physiologically inert and whose individual constituents are suitable for pharmaceuticals or foods. Importance is attached to the reciprocal physical-chemical affinity and compatibility between the coating material and the support film and this is always particularly good if the components used are identical or have similar characteristics. Whilst taking account of the active ingredient added, the coating compound formulation consequently corresponds to that given hereinbefore for the support film, the precise setting of the solids content and viscosity taking place by means of inert swelling and filling agents.

Thus, the material contains polymeric film forming agents, preferably gelatins and swelling or soluble starches, as well as optionally celluloses or hemicelluloses. In addition, plasticizers are added, particularly polyhydric alcohols, such as glycerol or sorbitol. In order to set the desired viscosity of the coating compound, which has the consistency of a slime, use is made of polymeric swelling agents, preferably alginates, pectins, chitins, lecithins or polyethylene glycols. These latter substances can simultaneously serve as adhesives. It is also possible to add water-soluble synthetic or natural resins or gums or gum Arabic, in order to improve the adhesion of the coating to the support material. It is finally possible to add preservatives, such as e.g. p-hydroxybenzoates, dyes (food dyes), pigments, such as titanium dioxide, or flavouring agents and sweeteners.

Coating materials with a water content of approximately 50% and a viscosity of approximately 30 to 10,000 cPs have proved particularly satisfactory. The formulation and production is similar to that of a pharmaceutical juice, in which the active ingredient or active ingredient combination is dissolved or uniformly dispersed. The coating material must have an adequate homogeneity and galenic stability, so that a uniform active ingredient content of the finished coating is ensured.

The following basic formulation has proved satisfactory:
  Gelatin 8 to 10 g
  Starch 3 to 8 g
  Glycerol 1 to 2 g
  Water 30 to 50 g The active ingredient is dissolved or dispersed in this basic material. When a dispersion is used, for uniform distribution purposes, the active ingredient must be extremely finely divided and preferably the average particle size is in the range approximately 1 to 20 μm.

The desired active ingredient dose and the sought surface of the dosage units determine the coating thickness, whilst account must be taken of the moisture content of the coating material and the finished coating.

The inventive administration form is particularly suitable for drugs, which are administered with a low dose rate, i.e. in which the individual dose for oral administration is between 0 mg (placebo) and approximately 20 mg. Suitable drug active ingredients occur in all fields of oral therapy, particular reference being made inter alia to analeptic, antibiotic, antidiabetic, antiemetic, antiepileptic, antihypertonic, corticoid, geriatric, hypnotic, cardiac, hypostatic and bio-active ingredients.

Approximately 4 to 20 g of active ingredient per $m^2$ (=10,000 $cm^2$) of support film can be applied in one coating process, so that 10 $cm^2$ (=2 standard postage stamps) can absorb up to 20 mg of active ingredient.

The coating material is normally applied to one side of the support film, but it is also possible to coat both sides, particularly in the case of two different active ingredients.

Each coating can contain one or more drug active ingredients. If, when using several active ingredients, they are not readily compatible with one another and cannot be contained in one coating material, it is possible in the case of the administration form according to the invention to apply the coating in the form of several individual coatings with different compositions and to separate the active ingredients from one another in this way; if necessary an active ingredient-free intermediate coating being provided. It is also possible to provide above the active ingredient-containing coating, a further protective coating, which protects the active ingredient or ingredients against contact with the atmosphere and/or light. In such cases, the protective coating must consequently be impermeable to air and moisture and/or must be made impermeable to light by the addition of corresponding dyes or pigments.

Through a corresponding build-up of the coating, it is possible to control the supply of active ingredient following the administration of the drug. For example, it is possible to place an active ingredient coating between at least two further coatings, which control the active ingredient resorption in the gastrointestinal tract in per se known manner. The active ingredient coating can e.g. be located between two acid-insoluble coatings, so that on administration it passes through the stomach and resorption only takes place in the gastric tract. In a similar way, different active ingredients can be superimposed in different coatings on the support film, so that resorption takes place successively and/or in delayed form.

Similar pharmacokinetic effects can be obtained through the incorporation (e.g. suspension) of differently pre-prepared microencapsulated active ingredients.

Coating of the support material with the active ingredient-containing coating material takes place by means of a roll application or coating process. This process, which is particularly suitable for quantitative coating, operates according to a process similar to intaglio printing and which is called "Akkugravur". Suitable machines are commercially available (Pagendarm, Hamburg) and permit application or coating weights of up to 80 g/$m^2$ in the case of web speeds of several 100 m/min. The reproducible constant weight is only ±2.5% for 20 g/$m^2$ and approximately ±10% for 1 g/$m^2$ over entire surface. The coating material is applied continuously by means of rollers with a special fine engraving, the engraved grooves forming an angle of 30 to 60, particularly 45° to the direction of movement of the support film. 27 to 80 grooves/cm can be etched into the rollers. Corresponding to its shape and depth, the engraving can absorb a given quantity of coating material and subsequently supply it to the support film. By varying the advance rate, running direction and engraving, as well as indirect application by means of a further speed-variable roller, it is possible to very accurately adjust the coating quantities.

A two-sided coating frequently gives advantages, because problems due to the warping of the support material and differing hygroscopicity are compensated. Multiple and even strip coatings and in fact even printing style coatings are possible and offer a considerable variability when processing incompatible active ingredients.

Another suitable application process corresponds to the coating of paper or films. Raw papers are improved in that they are coated with coating materials on one or both sides. The aqueous coating materials initially pass onto a rolling mill, which receives same by means of a rotary roller, strips same to a clearly defined coating thickness with a doctor blade at a given spacing and then the roller supplies the coating material to the support. The support film, which has a width of 0.30 to 7.50 m, subsequently passes through a drying tunnel and is wound onto reels. This process can be repeated on one or both sides in one or more stages and an already coated surface can be coated again. The weight of the support material increases by that of the dry weight. The accuracy of the application process using this doctor blade method is reproducibly ±5% and is dependent on the coating thickness, which can vary between 4 and 40 g/$m^2$. Within the individual production runs, it is possible to achieve a weight tolerance per surface unit down to ±1%.

When applying several coatings, as described hereinbefore, they are successively applied and optionally each coating previously passes through a drying station. This can e.g. comprise a temperature-controlled pair of rollers and a drying tunnel which is controllable in sections. Following the final coating process, the coating material is wound onto reels.

The active ingredient-coated support film is subsequently pre-divided into dosage units, which can be separated in much the same way as postage stamps. This pre-dividing is normally carried out by the drug manufacturer, but it is also conceivable to supply the coated material, e.g. to hospitals or pharmacists, where the pre-dividing can then be carried out in dose-dependent manner, or individually in accordance with information supplied by the doctor.

Pre-dividing takes place in a very simple manner by perforation or punching, it being possible to combine this step with the printing of the support material. In many cases it is more advantageous to carry out the printing of the support material prior to coating.

Before or preferably after pre-division of the active ingredient-coating into dosage units, the coated support material is cut into ready-for-use portions containing a given number of dosage units. It is also possible to cut the material on reels into narrow strips. It is then possible to separate the individual dosage units from the reel in much the same way as individual postage stamps.

As mainly natural substances, such as starches and gelatin are used as basic substances for producing the inventive administration form, products are obtained, which are similar to known wafers and whose oral ingestion presents no problems. It is important that the finished product is largely free from water, i.e. has a water content of less than 10 and preferably less than 2%, because otherwise mould can form.

The invention has been largely described hereinbefore in connection with drugs, but is in no way limited thereto. For example, it is also possible to adopt the same procedure for dosage forms for chemical reagents, flavouring substances and the like.

The following examples serve to further illustrate the invention.

EXAMPLE

Preparation of a drug administration form in the form of a coated film.

The following composition was used for producing a water-soluble support film:

| Gelatin | 10.0 parts by weight = 25% |
| Potato starch | 8.0 parts by weight = 20% |
| Glycerol | 1.5 parts by weight = 3.75% |
| Purified water | 20.5 parts by weight = 51.25% |

The viscosity of the slime-like composition was approximately 3000 cPs at 50° C. With the aid of a coating process, the material was processed to a film which, after drying, had a 9.3% residual water content.

Using the same basic substances as for the support film, the coating material was prepared in accordance with the following formulation:

| Gelatin | 10.0 parts by weight = 18.2% |
| Potato starch | 5.0 parts by weight = 9.1% |
| Glyercol | 1.0 parts by weight = 1.8% |
| Active ingredient | 5.0 parts by weight = 9.1% |
| Purified water | 34.0 parts by weight = 61.8% |

The viscosity of the slime-like composition was between 4000 and 10000 cPs, as a function of the temperature and active ingredient. To produce the coating material, the gelatin was firstly dissolved in an adequate quantity of water, whereby firstly water at 90° to 95° C. was provided and into which the gelatin was introduced, accompanied by stirring. The active ingredient was dissolved together with the glycerol in water in a separate mixture. Finally, the potato starch was mixed in an adequate quantity of water at 50° to 60° C. and accompanied by stirring. The gelatin solution and potato starch suspension were added together and the active ingredient suspension was slowly stirred into the mixture, whilst avoiding air inclusions.

The temperature was kept at 55° to 60° C. Finally, the desired water content was adjusted by adding further water.

By means of Akkugravur, the coating material was applied to the support film with a wet coating weight of 55 g/m². After drying, the coating weight was 23 g/m², corresponding to an active ingredient content of 5 g/m². The active ingredient-coated film was then perforated in box-like manner, so that the individual portions have a surface of 5 cm², in the case of dimensions of 2×2.5 cm, such a portion containing 2.5 mg of active ingredient. The residual moisture content of the product was 8.6% after drying.

An administration form was obtained, which on oral administration rapidly swells and dissolves in the mouth and can therefore be easily swallowed.

I claim:
1. In a process for the production of an administration and dosage form for drugs, reagents or other active ingredients in the form of a film with an active ingredient-containing coating, in which process
   (a) a water-soluble support film is produced from an aqueous composition based on an effective amount of a compound selected from starches, gelatins, and their mixtures and an effective amount of a compound selected from glycerol, sorbitol and their mixtures,
   (b) an aqueous coating material is prepared from an effective amount of the active ingredient, as well as an effective amount of a compound selected from starches, gelatins, and their mixtures and an effective amount of a compound selected from glycerol, sorbitol and their mixtures, and
   (c) the coating material is continuously applied by means of a roll coating process and in a precisely predetermined quantity to at least one side of the support film,
the improvement that the basic composition of the support film corresponds to that of the coating material.

2. Process according to claim 1, characterized in that the support film and the coating material also comprises a substance selected from the group comprising natural and synthetic resins and gums and their mixtures.

3. Process according to claim 1, characterized in that the composition of the support film contains further additives selected from the group consisting of inert soluble and insoluble fillers, sugar and other sweeteners, plasticizers such as polyols, waxes and dyes, flavouring substances and preservatives.

4. Process according to claim 1, characterized in that the coating material contains further additives selected from the group consisting of soluble and insoluble fillers, sugar and other sweeteners, plasticizers such as polyols, waxes and dyes, flavouring substances and preservatives.

5. Process according to claim 1, characterized in that the coating compound is applied to the support film in a continuous manner by means of grooved rollers, which absorb a clearly defined quantity of coating material and then transfer it to the support film.

6. Process according to claim 1, characterized in that the coating material is continuously applied to the support film by means of smooth roller pairs, which in speed-displaced synchronism absorb the material and transfer it to the support film in a clearly defined quantity.

7. Process according to claim 1, characterized in that the composition of the support film and of the coating material comprises 8 to 10 parts by weight of gelatin, 4 to 8 parts by weight of starch, 1 to 2 parts by weight of glycerol and 20 to 50 parts by weight of water.

8. Process according to claim 7, characterized in that the coating material comprises up to 10 parts by weight of the active ingredient.

9. Process according to claim 1, characterized in that different active ingredients are applied to the top and bottom surfaces of the support film for producing a combination product.

10. Process according to claim 1, characterized in that a coating material is used which comprises more than one active ingredient.

11. Process according to claim 1, characterized in that mutually incompatible active ingredients are applied in the form of separate coatings to the support film and an ingredient-free intermediate coating is provided between the two ingredient-containing coatings.

12. Process according to claim 1, characterized in that an active ingredient coating is placed between at least two further coatings, which control the active ingredient resorption in the gastrointestinal tract and one of the coatings can be the support film.

13. Process according to claim 1, characterized in that a further coating is placed over the active ingredient coating and protects the active ingredient against contact with the atmosphere, against light or against both.

14. Process according to claim 1, characterized in that the active ingredient-coated water-soluble film is subdivided into portions by perforation or punching and said portions contain defined dosage units of the active ingredient.

15. Process according to claim 1, characterized in that the back of the support material is printed with the active ingredient composition or information relating to its medical application.

* * * * *